United States Patent
Lechner et al.

(10) Patent No.: US 10,251,821 B2
(45) Date of Patent: Apr. 9, 2019

(54) OXIDIZING COLORANT

(71) Applicant: Henkel AG & Co. KGaA, Duesseldorf (DE)

(72) Inventors: Torsten Lechner, Langenfeld (DE); Aileen Wagner, Hamburg (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/613,249

(22) Filed: Jun. 4, 2017

(65) Prior Publication Data

US 2017/0266086 A1 Sep. 21, 2017

Related U.S. Application Data

(63) Continuation of application No. PCT/EP2015/074948, filed on Oct. 28, 2015.

(30) Foreign Application Priority Data

Dec. 3, 2014 (DE) .......... 10 2014 224 804

(51) Int. Cl.
| | | |
|---|---|---|
| *A61Q 5/10* | (2006.01) | |
| *A61K 8/22* | (2006.01) | |
| *A61K 8/34* | (2006.01) | |
| *A61K 8/46* | (2006.01) | |
| *A61K 8/73* | (2006.01) | |
| *A61K 8/86* | (2006.01) | |
| *A61K 8/92* | (2006.01) | |
| *A61K 8/19* | (2006.01) | |

(52) U.S. Cl.
CPC ............ *A61K 8/22* (2013.01); *A61K 8/19* (2013.01); *A61K 8/342* (2013.01); *A61K 8/463* (2013.01); *A61K 8/731* (2013.01); *A61K 8/86* (2013.01); *A61K 8/922* (2013.01); *A61Q 5/10* (2013.01); *A61K 2800/4324* (2013.01); *A61K 2800/882* (2013.01)

(58) Field of Classification Search
CPC .......... A61Q 5/10; A61K 8/342; A61K 8/463; A61K 8/731; A61K 8/22; A61K 8/922; A61K 8/19; A61K 8/86; A61K 2800/4324; A61K 2800/882

See application file for complete search history.

(56) References Cited

U.S. PATENT DOCUMENTS

| | | |
|---|---|---|
| 2007/0169285 A1 | 7/2007 | Naraslmhan et al. |
| 2010/0307527 A1 | 12/2010 | Bureiko et al. |
| 2012/0305416 A1* | 12/2012 | Miyabe ............... A45D 34/00 206/223 |
| 2015/0315177 A1 | 11/2015 | Rudolph et al. |

FOREIGN PATENT DOCUMENTS

| | | |
|---|---|---|
| CA | 2573567 A1 | 3/2006 |
| DE | 19756454 C1 | 6/1999 |
| EP | 1642563 A2 | 8/2005 |
| WO | 2005065632 A1 | 7/2005 |
| WO | 2015018412 A2 | 2/2015 |

OTHER PUBLICATIONS

PCT International Search Report (PCT/EP2015/074948) dated Dec. 16, 2015.

* cited by examiner

*Primary Examiner* — Eisa B Elhilo
(74) *Attorney, Agent, or Firm* — James J. Cummings

(57) ABSTRACT

A composition for oxidatively treating hair includes—50-96 wt. % water; 0.5-20 wt. % hydrogen peroxide; at least one linear saturated 1-alkanol with 12-30 carbon atoms in a total volume of 2.7-6 wt. %; at least one polyethylene glycol ether of a linear saturated C12-C22 alkanol with 15-30 ethylene oxide units in the molecule, in a total volume of 0.3-1 wt. %; at least one anionic surfactant in a total volume of 0.3-1 wt. %; at least one cellulose ether in a total volume of 0.1-0.5 wt. %; and at least one oil in a total volume of 0.1-0.5 wt. %. The composition is highly suitable as an oxidant for powdered color preparations, containing oxidizing coloring intermediates and also pigments, which do not permanently change the color of the fibers, as well as, optionally, including solid inorganic alkalizing agents, as well as, optionally, ammonium salts, like ammonium chloride and ammonium sulfate, in particular with respect to the application properties of the application mixture.

15 Claims, No Drawings

OXIDIZING COLORANT

FIELD OF THE INVENTION

The present invention generally relates to compositions which are suitable as oxidizing agents for powdered dyeing preparations, which include oxidation dye precursors and also pigments, but do not permanently change the color of the fibers, and optionally solid inorganic alkalizing agents, and optionally furthermore ammonium salts.

The present invention also generally relates to agents for changing the color of keratin fibers, which can be produced from two separate compositions by mixing the two compositions, wherein one of the two compositions is an oxidative composition according to the first subject matter of the application, and the second composition is a powdered dyeing preparation, which comprises at least one oxidation dye precursor and at least one pigment that does not permanently change the color of the fibers.

The present invention also generally relates to a kit for an oxidation dye for permanently changing the color of keratin fibers, comprising a powdered dye preparation and an aqueous hydrogen peroxide preparation, wherein the hydrogen peroxide preparation is optimized to the effect that the ready-to-use mixture made of powder and hydrogen peroxide preparation represents a viscous paste that is easy to apply to the fibers to be dyed and remains there during the application duration of 10 to 60 minutes, without dripping off the hair prematurely in significant amounts.

A further subject matter of the present invention relates a method for oxidatively changing the color of keratin fibers, wherein the ready-to-apply dye is produced by mixing the components of the aforementioned kit prior to application.

BACKGROUND OF THE INVENTION

A person skilled in the art knows a variety of methods for changing the color of human hair. In general, either substantive dyes or oxidation dyes are used to dye human hair, which are created by oxidatively coupling one or more developer components among one another or to one or more coupler components. The coupler and developer components are also referred to as oxidation dye precursors. The colorations achieved with oxidation dyes are typically referred to as permanent or semi-permanent colorations.

These agents usually comprise hydrogen peroxide as the oxidizing agent. Since hydrogen peroxide is only insufficiently storage-stable in the alkaline pH range, oxidative dyes are usually composed of two components, which are mixed with one another immediately before being applied. The one component comprises hydrogen peroxide in an aqueous solution or emulsion, wherein this composition has an acid pH value in the range of 3 to 5.5 to stabilize the hydrogen peroxide. The second component includes the dye precursors and one or more alkalizing agents in an amount such that the application mixture composed of the two components has a pH value in the range of 8 to 11. In addition, dyeing kits and dyeing methods are available, in which the application mixture composed of the two components has a pH value in the range of approximately 6 to 7.9; the coloring result of these so-called "acid" colorations, however, frequently do not achieve the quality attained with alkaline application mixtures.

The dye component is usually present in the form of an emulsion or gel of approximately 20 to 85 wt. %. However, dyeing kits in which the dye component is present in powdered form are also available. Advantages of these powders are that the oxidation dye precursors are present in solid form, and not in solute form, and consequently do not have to be stabilized to the same degree as dyeing emulsions or dyeing gels to prevent premature oxidation. Dyeing powders are also technologically less complex and less expensive to produce than dyeing emulsions and gels.

Powdered oxidation dye precursors can clump during extended storage, which makes it more difficult to produce a homogeneous application mixture from the powder and the aqueous oxidizing agent preparation. For this reason, a flow aid or an anti-caking agent is typically added to the dye powders, which itself is not water-soluble, such as silica. In addition, dyeing kits comprising dye powders and oxidizing agent preparations are available in the market, in which the dye powder comprises insoluble pigments that approximately reflect the color effect of the permanent hair color that is achieved. To oxidatively dye hair, the dye powder is mixed with an aqueous oxidizing agent preparation, for example in a bottle or a shaker cap, and the resulting cream-like application mixture is applied to the hair to be dyed, where it remains for a residence time of 5 to 60 minutes before being rinsed off again.

These products can be subject to the drawback that the application mixture, which represents a dispersion of the insoluble powder components in the aqueous oxidizing agent preparation, separates into solid and liquid components already before the recommended residence time has lapsed, thereby losing viscosity and dripping off the hair.

It is therefore desirable to provide an improved oxidizing agent preparation for oxidative dyes made of dye powders and oxidizing agents, which allows stable powder dispersions to be produced that have sufficient viscosity during the entire residence time and remain on the hair without dripping off. Furthermore, other desirable features and characteristics of the present invention will become apparent from the subsequent detailed description of the invention and the appended claims, taken in conjunction with this background of the invention.

BRIEF SUMMARY OF THE INVENTION

A first subject matter of the present invention is thus an oxidation composition for oxidatively treating hair, which includes:
  50 to 96 wt. % water;
  0.5 to 20 wt. % hydrogen peroxide;
  at least one linear saturated 1-alkanol having 12 to 30 carbon atoms in a total amount of 2.7 to 6 wt. %;
  at least one polyethylene glycol ether of a linear saturated C12-C22 alkanol having 15 to 30 ethylene oxide units in the molecule, in a total amount of 0.3 to 1 wt. %;
  at least one anionic surfactant in a total amount of 0.3 to 1 wt. %;
  at least one cellulose ether in a total amount of 0.1 to 0.5 wt. %; and
  at least one oil in a total amount of 0.1 to 0.5 wt. %;
wherein all quantity information is based on the weight of the oxidation composition.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Surprisingly, it was found that aqueous hydrogen peroxide preparations, comprising at least one fatty alcohol, one or more certain fatty ethoxylates, at least one anionic surfactant, at least one cellulose ether, each in select quantity ranges, and small amounts of at least one oil achieve the object at hand very well.

The oxidation composition according to the invention preferably comprises, based on the weight thereof, 50 to 96 wt. %, preferably 70 to 93 wt. %, and particularly preferably 80 to 90 wt. % water.

The oxidation composition according to the invention preferably comprises, based on the weight thereof, 0.5 to 20 wt. %, preferably 1 to 12 wt. %, and particularly preferably 3 to 6 wt. % hydrogen peroxide.

The oxidation composition according to the invention comprises, based on the weight thereof, at least one linear saturated 1-alkanol having 12 to 30 carbon atoms in a total amount of 2.7 to 6 wt. %, preferably in a total amount of 3 to 5.5 wt. %, and particularly preferably in a total amount of 3.5 to 4.5 wt. %.

The at least one linear saturated 1-alkanol having 12 to 30 carbon atoms is preferably selected from myristyl alcohol, cetyl alcohol, stearyl alcohol, arachidyl alcohol and behenyl alcohol, and mixtures of these alkanols, and preferably from cetyl alcohol, stearyl alcohol and cetyl alcohol/stearyl alcohol mixtures. Preferred oxidation compositions according to the invention comprise, based on the weight thereof, a cetyl alcohol/stearyl alcohol mixture in a total amount of 2.7 to 6 wt. %, preferably in a total amount of 3 to 5.5 wt. %, and particularly preferably in a total amount of 3.5 to 4.5 wt. %.

The oxidation composition according to the invention comprises, based on the weight thereof, at least one polyethylene glycol ether of a linear saturated C12-C22 alkanol having 15 to 30 ethylene oxide units in the molecule, in a total amount of 0.3 to 1 wt. %, preferably 0.4 to 0.8 wt. %, and particularly preferably 0.5 to 0.7 wt. %.

The at least one polyethylene glycol ether is preferably selected from polyethylene glycol ethers of lauryl alcohol, myristyl alcohol and cetyl alcohol, each having 15 to 30 ethylene oxide units in the molecule, and particularly preferably is selected from Laureth-23.

Particularly preferred oxidation compositions according to the invention comprise, based on the weight thereof, at least one polyethylene glycol ether of lauryl alcohol, myristyl alcohol or cetyl alcohol, each having 15 to 30 ethylene oxide units in the molecule, in a total amount of 0.3 to 1 wt. %, preferably 0.4 to 0.8 wt. %, and particularly preferably 0.5 to 0.7 wt. %. Exceptionally preferred oxidation compositions according to the invention comprise, based on the weight thereof, Laureth-23 in a total amount of 0.3 to 1 wt. %, preferably 0.4 to 0.8 wt. %, and particularly preferably 0.5 to 0.7 wt.

The oxidation composition according to the invention comprises, based on the weight thereof, at least one anionic surfactant in a total amount of 0.3 to 1 wt. %, preferably 0.4 to 0.8 wt. %, and particularly preferably 0.5 to 0.7 wt.

The at least one anionic surfactant is preferably selected from the sodium salts of fatty alcohol sulfates, and preferably is selected from sodium cetyl sulfate, sodium stearyl sulfate and sodium cetyl/stearyl sulfate mixtures.

Particularly preferred oxidation compositions according to the invention comprise, based on the weight thereof, at least one anionic surfactant, selected from the sodium salts of fatty alcohol sulfates, and preferably selected from sodium cetyl sulfate, sodium stearyl sulfate and sodium cetyl/stearyl sulfate mixtures, in a total amount of 0.3 to 1 wt. %, preferably 0.4 to 0.8 wt. %, and particularly preferably 0.5 to 0.7 wt. %.

The oxidation composition according to the invention comprises, based on the weight thereof, at least one cellulose ether in a total amount of 0.1 to 0.5 wt. %, preferably 0.2 to 0.4 wt. %, and particularly preferably 0.25 to 0.3 wt.

The at least one cellulose ether is preferably selected from hydroxyethyl cellulose, hydroxypropyl cellulose, hydroxypropyl methyl cellulose, methyl hydroxyethyl cellulose and mixtures thereof, and particularly preferably is selected from hydroxyethyl cellulose.

Particularly preferred oxidation compositions according to the invention comprise, based on the weight thereof, at least one cellulose ether, selected from hydroxyethyl cellulose, hydroxypropyl cellulose, hydroxypropyl methyl cellulose, methyl hydroxyethyl cellulose and mixtures thereof, and particularly preferably selected from hydroxyethyl cellulose, in a total amount of 0.1 to 0.5 wt. %, preferably 0.2 to 0.4 wt. %, and particularly preferably 0.25 to 0.3 wt. %.

The oxidation composition according to the invention comprises, based on the weight thereof, at least one oil in a total amount of 0.1 to 0.5 wt. %, and preferably 0.2 to 0.4 wt. %.

Preferred oils according to the invention are selected from natural and synthetic hydrocarbons, and particularly preferably from paraffin oils, $C_{18}$ to $C_{30}$ isoparaffins, in particular isoeicosane, polyisobutene and polydecene, which are available under the designation Emery® 3004, 3006, 3010 or under the designation Ethylflo® from Albemarle or Nexbase® 2004G from Nestle, for example, and further selected from $C_8$ to $C_{16}$ isoparaffins, in particular from isodecane, isododecane, isotetradecane and isohexadecane, and mixtures thereof, as well as 1,3-bis(2-ethylhexyl)cyclohexane (available under the trade name Cetiol® S from BASF, for example).

Further preferred oils according to the invention are selected from the benzoic acid esters of linear or branched C8-22 alkanols. Particularly preferred are benzoic acid-$C_{12}$-$C_{15}$-alkyl esters, for example available as the commercial product Finsolv® TN, benzoic acid isostearyl esters, for example available as the commercial product Finsolv® SB, ethylhexyl benzoate, for example available as the commercial product Finsolv® EB, and benzoic acid 2-octyldodecyl esters, for example available as the commercial product Finsolv® BOD.

Further preferred oils according to the invention are selected from fatty alcohols having 6 to 30 carbon atoms, which are unsaturated, or branched and saturated, or branched and unsaturated. The branched alcohols are frequently also referred to as Guerbet alcohols since they can be obtained by way of the Guerbet reaction. Preferred alcohol oils are 2-hexyldecanol (Eutanol® G 16), 2-octyldodecanol (Eutanol® G), 2-ethylhexyl alcohol and isostearyl alcohol.

Further preferred oils are selected from mixtures of Guerbet alcohols and Guerbet alcohol esters, for example the commercial product Cetiol® PGL (2-hexyldecanol and 2-hexyldecyl laurate).

Further preferred cosmetic oils according to the invention are selected from the triglycerides (=triple esters of glycerol) of linear or branched, saturated or unsaturated, optionally hydroxylated C8-30 fatty acids. The use of natural oils can be particularly preferred, such as amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, currant seed oil, jojoba oil, linseed oil, macadamia nut oil, corn oil, almond oil, marula oil, evening primrose oil, olive oil, palm oil, palm kernel oil, Brazil nut oil, pecan nut oil, peach kernel oil, rapeseed oil, castor oil, sea buckthorn pulp oil, sea buckthorn kernel oil, sesame oil, soy bean oil, sunflower oil, grape seed oil, walnut oil, wild rose oil, wheat germ oil, and the liquid components of coconut oil, and the like. However, synthetic triglyceride oils, in particular capric/caprylic triglycerides, such as the commercial products Myritol® 318, Myritol® 331 (BASF) or Miglyol® 812 (Hüls) comprising unbranched fatty acid esters and glyceryl triisostearin with branched fatty acid esters are also preferred.

Further particularly preferred cosmetic oils according to the invention are selected from the dicarboxylic acid esters of linear or branched $C_2$ to $C_{10}$ alkanols, in particular diisopropyl adipate, di-n-butyl adipate, di-(2-ethylhexyl) adipate, dioctyl adipate, diethyl-/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl) succinate.

Further particularly preferred cosmetic oils according to the invention are selected from the esters of the linear or branched, saturated or unsaturated fatty alcohols having 2 to 30 carbon atoms with linear or branched, saturated or unsaturated fatty acids having 2 to 30 carbon atoms, which may be hydroxylated. These include 2-hexyldecyl stearate (Eutanol® G 16 S), 2-hexyldecyl laurate, isodecyl neopentanoate, isononyl isononanoate, 2-ethylhexyl palmitate (Cegesoft® C 24) and 2-ethylhexyl stearate (Cetiol® 868). Likewise preferred are isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate, and ethylene glycol dipalmitate.

Further preferred cosmetic oils according to the invention are selected from the addition products of 1 to 5 propylene oxide units to monohydric or polyhydric $C_{8-22}$ alkanols, such as octanol, decanol, decanediol, lauryl alcohol, myristyl alcohol, and stearyl alcohol, such as PPG-2 myristyl ether and PPG-3 myristyl ether (Witconol® APM).

Further preferred cosmetic oils according to the invention are selected from the addition products of at least 6 ethylene oxide units and/or propylene oxide units to monohydric or polyhydric $C_{3-22}$ alkanols, such as glycerol, butanol, butanediol, myristyl alcohol and stearyl alcohol, which may optionally be esterified, such as PPG-14 butyl ether (Ucon Fluid® AP), PPG-9 butyl ether (Breox® B25), PPG-10 butanediol (Macol® 57), PPG-15 stearyl ether (Arlamol® E), and glycereth-7-diisononanoate.

Further preferred cosmetic oils according to the invention are selected from the $C_8$ to $C_{22}$ fatty alcohol esters of monovalent or polyvalent $C_2$ to $C_7$ hydroxycarboxylic acids, in particular the esters of glycolic acid, lactic acid, malic acid, tartaric acid, citric acid, and salicylic acid. Such esters based on linear $C_{14/15}$ alkanols, such as $C_{12}$-$C_{15}$ alkyl lactate, and of $C_{12/13}$ alkanols branched at the 2-position, may be purchased under the trademark Cosmacol® from Nordmann, Rassmann GmbH & Co., Hamburg, in particular the commercial products Cosmacol® ESI, Cosmacol® EMI, and Cosmacol® ETI.

Further preferred cosmetic oils according to the invention are selected from the symmetric, asymmetric or cyclic esters of carbonic acid with $C_{3-22}$ alkanols, $C_{3-22}$ alkane diols or $C_{3-22}$ alkane triols, such as dicaprylyl carbonate (Cetiol® CC), or the esters according to the teaching of DE 19756454 A1, and in particular glycerol carbonate.

Further cosmetic oils that may be preferred according to the invention are selected from the esters of dimers of unsaturated $C_{12}$ to $C_{22}$ fatty acids (dimer fatty acids) with monohydric linear, branched or cyclic $C_2$ to $C_{18}$ alkanols or polyhydric linear or branched $C_2$ to $C_6$ alkanols.

Further cosmetic oils that are suitable according to the invention are selected from silicone oils, which also include, for example, dialkyl and alkyaryl siloxanes, such as cyclopentasiloxane, cyclohexasiloxane, dimethylpolysiloxane and methylphenylpolysiloxane, but also hexamethyldisiloxane, octamethyltrisiloxane and decamethyltetrasiloxane. Volatile silicone oils, which may be cyclic, can be preferred, such as octamethylcyclotetrasiloxane, decamethylcyclopentasiloxane and dodecamethylcyclohexasiloxane, and mixtures thereof, as they can be found in the commercial products DC 244, 245, 344 and 345 from Dow Corning, for example. Volatile linear silicone oils are likewise suitable, in particular hexamethyldisiloxane ($L_2$), octamethyltrisiloxane ($L_3$), decamethyltetrasiloxane ($L_4$), and arbitrary mixtures of two and three of $L_2$, $L_3$ and/or $L_4$, preferably mixtures such as those present, for example, in the commercial products DC 2-1184, Dow Corning® 200 (0.65 cSt) and Dow Corning® 200 (1.5 cSt) from Dow Corning. Preferred non-volatile silicone oils are selected from higher molecular weight linear dimethylpolysiloxanes, commercially available, for example, under the designation Dow Corning® 190, Dow Corning® 200 Fluid having kinematic viscosities (25° C.) in the range of 5 to 100 cSt, preferably 5 to 50 cSt, or 5 to 10 cSt, and dimethylpolysiloxane having a kinematic viscosity (25° C.) of approximately 350 cSt.

It may be exceptionally preferred according to the invention to use mixtures of the aforementioned oils.

Preferred oxidation compositions according to the invention are characterized in that the cosmetic oil is selected from natural and synthetic hydrocarbons, and particularly preferably from paraffin oils, $C_{18}$ to $C_{30}$ isoparaffins, in particular isoeicosane, polyisobutenes and polydecenes, $C_8$ to $C_{16}$ isoparaffins, and 1,3-bis(2-ethylhexyl)cyclohexane; the benzoic acid esters of linear or branched $C_{8-22}$ alkanols; fatty alcohols having 6 to 30 carbon atoms, which are unsaturated, or branched and saturated, or branched and unsaturated; triglycerides of linear or branched, saturated or unsaturated, optionally hydroxylated $C_{8-30}$ fatty acids, and in particular natural oils; the dicarboxylic acid esters of linear or branched $C_2$ to $C_{10}$ alkanols, the esters of linear or branched saturated or unsaturated fatty alcohols having 2 to 30 carbon atoms with linear or branched saturated or unsaturated fatty acids having 2 to 30 carbon atoms, which may be hydroxylated; the addition products of 1 to 5 propylene oxide units to monohydric or polyhydric $C_{8-22}$ alkanols; the addition products of at least 6 ethylene oxide and/or propylene oxide units to monohydric or polyhydric $C_{3-22}$ alkanols; the $C_8$ to $C_{22}$ fatty alcohol esters of monovalent or polyvalent $C_2$ to $C_7$ hydroxycarboxylic acids; the symmetric, asymmetric or cyclic esters of carbonic acid with $C_{3-22}$ alkanols, $C_{3-22}$ alkane diols or $C_{3-22}$ alkane triols; the esters of dimers of unsaturated $C_{12}$ to $C_{22}$ fatty acids (dimeric fatty acids) with monohydric linear, branched or cyclic $C_2$ to $C_{18}$ alkanols or with polyhydric linear or branched $C_2$ to $C_6$ alkanols; silicone oils and mixtures of the aforementioned substances.

The oxidation composition according to the invention preferably has a viscosity in the range of 1000 to 600 mPa·s, and particularly preferably 1500 to 3500 mPa·s, each measured at 22° C. using a Brookfield RV-T type viscometer with an LV-1 spindle or an RV-1 spindle and a speed of 30 revolutions/minute.

So as to stabilize the oxidizing agent during storage, it is in particular preferred if the oxidation composition according to the invention has an acid pH value, in particular a pH value in the range of 2.5 to 5.5, and preferably of 3.0 to 5.0. Preferred acidifying agents are food-grade acids such as citric acid, acetic acid, malic acid or tartaric acid, and diluted mineral acids, and in particular phosphoric acid.

It is preferred to use what are known as complexing agent so as to stabilize the oxidizing agent in the oxidation composition according to the invention. Complexing agents are substances that can form complexes with metallic ions. Preferred complexing agents are the so-called chelating agents, which is to say substances that are capable of binding metal ions to form cyclic compounds, where a single ligand occupies more than one coordination site on a central atom. The number of bound ligands depends on the coordination number of the central ion. Common chelating agents, which are preferred within the scope of the present invention, are, for example, polyoxycarboxylic acids, polyamines, ethylenediaminetetraacetic acid (EDTA), nitrilotriacetic acid (NTA), and hydroxyethane diphosphonic acids or the alkali salts thereof. Preferred complexing agents according to the invention are phosphonates, preferably hydroxyalkane or aminoalkane phosphonates, and in particular 1-hydroxyethane-1,1-diphosphonate (HEDP) or the disodium or tetrasodium salt thereof and/or ethylenediamine tetramethylene phosphonate (EDTMP) or the hexasodium salt thereof and/or diethylenetriamine pentamethylene phosphonate (DTPMP) or the heptasodium or octasodium salt thereof. Dipicolinic acid is also preferably used as a complexing agent according to the invention. Agents that comprise a combination of an EDTA salt and HEDP and dipicolinic acid are particularly preferred according to the invention.

Further preferred oxidation compositions according to the invention are composed as follows, wherein all quantity information is based on the weight of the oxidation composition:
50 to 96 wt. % water;
0.5 to 20 wt. % hydrogen peroxide;
at least one linear saturated 1-alkanol having 12 to 30 carbon atoms in a total amount of 2.7 to 6 wt. %;
at least one polyethylene glycol ether of a linear saturated C12-C22 alkanol having 15 to 30 ethylene oxide units in the molecule, in a total amount of 0.3 to 1 wt. %;
at least one anionic surfactant in a total amount of 0.3 to 1 wt. %;
at least one cellulose ether in a total amount of 0.1 to 0.5 wt. %; and
at least one oil in a total amount of 0.1 to 0.5 wt. %;
wherein 3 to 5.5 wt. % cetearyl alcohol;
0.3 to 1 wt. % Laureth-23;
0.3 to 1 wt. % sodium cetearyl sulfate; and
0.1 to 0.5 wt. % hydroxyethyl cellulose are present;
80 to 96 wt. % water;
0.5 to 20 wt. % hydrogen peroxide;
at least one linear saturated 1-alkanol having 12 to 30 carbon atoms in a total amount of 2.7 to 6 wt. %;
at least one polyethylene glycol ether of a linear saturated C12-C22 alkanol having 15 to 30 ethylene oxide units in the molecule, in a total amount of 0.3 to 1 wt. %;
at least one anionic surfactant in a total amount of 0.3 to 1 wt. %;
at least one cellulose ether in a total amount of 0.1 to 0.5 wt. %; and
at least one oil in a total amount of 0.1 to 0.5 wt. %;
wherein 3.5 to 4.5 wt. % cetearyl alcohol;
0.4 to 0.8 wt. % Laureth-23;
0.3 to 1 wt. % sodium cetyl sulfate;
0.1 to 0.5 wt. % hydroxyethyl cellulose are present;
80 to 96 wt. % water;
0.5 to 20 wt. % hydrogen peroxide;
at least one linear saturated 1-alkanol having 12 to 30 carbon atoms in a total amount of 2.7 to 6 wt. %;
at least one polyethylene glycol ether of a linear saturated C12-C22 alkanol having 15 to 30 ethylene oxide units in the molecule, in a total amount of 0.3 to 1 wt. %;
at least one anionic surfactant in a total amount of 0.3 to 1 wt. %;
at least one cellulose ether in a total amount of 0.1 to 0.5 wt. %; and
at least one oil in a total amount of 0.1 to 0.5 wt. %;
wherein 3.5 to 4.5 wt. % cetearyl alcohol;
0.4 to 0.8 wt. % Laureth-23;
0.3 to 1 wt. % sodium stearyl sulfate;
0.1 to 0.5 wt. % hydroxyethyl cellulose are present;
80 to 96 wt. % water;
0.5 to 20 wt. % hydrogen peroxide;
at least one linear saturated 1-alkanol having 12 to 30 carbon atoms in a total amount of 2.7 to 6 wt. %;
at least one polyethylene glycol ether of a linear saturated C12-C22 alkanol having 15 to 30 ethylene oxide units in the molecule, in a total amount of 0.3 to 1 wt. %;
at least one anionic surfactant in a total amount of 0.3 to 1 wt. %;
at least one cellulose ether in a total amount of 0.1 to 0.5 wt. %; and
at least one oil in a total amount of 0.1 to 0.5 wt. %;
wherein 3.5 to 4.5 wt. % cetearyl alcohol;
0.4 to 0.8 wt. % Laureth-23;
0.3 to 1 wt. % sodium stearyl sulfate;
0.1 to 0.5 wt. % hydroxypropyl cellulose are present;
50 to 96 wt. % water;
0.5 to 20 wt. % hydrogen peroxide;
at least one linear saturated 1-alkanol having 12 to 30 carbon atoms in a total amount of 2.7 to 6 wt. %;
at least one polyethylene glycol ether of a linear saturated C12-C22 alkanol having 15 to 30 ethylene oxide units in the molecule, in a total amount of 0.3 to 1 wt. %;
at least one anionic surfactant in a total amount of 0.3 to 1 wt. %;
at least one cellulose ether in a total amount of 0.1 to 0.5 wt. %; and
at least one oil in a total amount of 0.1 to 0.5 wt. %;
wherein 3 to 5.5 wt. % cetearyl alcohol;
0.3 to 1 wt. % Laureth-23;
0.3 to 1 wt. % sodium cetearyl sulfate; and
0.1 to 0.5 wt. % hydroxyethyl cellulose are present; and
the composition has a pH value in the range of 2.5 to 5.5 and a viscosity in the range of 1000 to 600 mPa·s, and preferably 1500 to 3500 mPa·s.

A further subject matter of the present invention is a kit for oxidatively changing the color of keratin fibers, comprising two compositions that are separate from one another, wherein one of the two compositions is an oxidation composition as described above, comprising:
50 to 96 wt. % water;
0.5 to 20 wt. % hydrogen peroxide;

at least one linear saturated 1-alkanol having 12 to 30 carbon atoms in a total amount of 2.7 to 6 wt. %;
at least one polyethylene glycol ether of a linear saturated C12-C22 alkanol having 15 to 30 ethylene oxide units in the molecule, in a total amount of 0.3 to 1 wt. %;
at least one anionic surfactant in a total amount of 0.3 to 1 wt. %;
at least one cellulose ether in a total amount of 0.1 to 0.5 wt. %; and
at least one oil in a total amount of 0.1 to 0.5 wt. %;
wherein all quantity information is based on the weight of the oxidation composition. and the second composition is a powdered dyeing preparation, which comprises at least one oxidation dye precursor and at least one pigment that does not permanently change the color of the fibers.

What was said above with respect to the oxidation composition according to the invention applies, mutatis mutandis, with respect to further preferred embodiments of the kit according to the invention.

A further subject matter of the present invention is a method for oxidatively changing the color of keratin fibers, characterized by the following method steps: providing an oxidation composition, comprising
50 to 96 wt. % water;
0.5 to 20 wt. % hydrogen peroxide;
at least one linear saturated 1-alkanol having 12 to 30 carbon atoms in a total amount of 2.7 to 6 wt. %;
at least one polyethylene glycol ether of a linear saturated C12-C22 alkanol having 15 to 30 ethylene oxide units in the molecule, in a total amount of 0.3 to 1 wt. %;
at least one anionic surfactant in a total amount of 0.3 to 1 wt. %;
at least one cellulose ether in a total amount of 0.1 to 0.5 wt. %; and
at least one oil in a total amount of 0.1 to 0.5 wt. %;
wherein all quantity information is based on the weight of the oxidation composition; and providing a powdered dyeing preparation, which comprises at least one oxidation dye precursor and at least one pigment that does not permanently change the color of the fibers; producing a mixture of the aforementioned oxidation composition and the aforementioned powdered dyeing preparation, preferably at a weight ratio of the oxidation composition to the powdered dyeing preparation of 6 to 12, particularly preferably of 8 to 11, and exceptionally preferably of 9 to 10; immediately thereafter, distributing the ready-to-apply agent on the fibers; leaving the agent on the fibers for a time period of 1 to 60 minutes; thereafter, rinsing the remaining agent from the fibers and optionally drying the hair.

The method according to the invention comprises the mixing of the liquid oxidation composition with a powdered dyeing preparation, which comprises at least one oxidation dye precursor and at least one pigment that does not permanently change the color of the fibers. The mixing of the two components preferably takes place in a reclosable container.

What was said above with respect to the oxidation composition according to the invention applies, mutatis mutandis, with respect to further preferred embodiments of the method according to the invention.

According to the invention, keratin fibers or keratin-containing fibers shall be understood to mean wool, furs, feathers, and in particular human hair. However, in principle, the dyeing and/or lightening methods according to the invention can also be used on other natural fibers, such as cotton, jute, sisal, linen, silk or modified natural fibers, such as regenerated cellulose, nitro cellulose, alkyl cellulose, or hydroxyalkyl cellulose, or acetyl cellulose.

In addition to the oxidation composition according to the invention, a powdered dyeing preparation, which comprises at least one oxidation dye precursor and at least one pigment that does not permanently change the color of the fibers, represents the second essential part of the kit according to the invention and of the method according to the invention.

According to the invention, the term "powdered" shall be understood to mean a flowable form of administration that is solid and composed of individual particles, in which the individual particles have particle sizes in the range of 0.1 µm to no more than 1 mm. Where necessary, the particles can be adapted to the requirements of the agents by physical treatment such as sifting, pressing, granulating or pelletizing, or by adding certain auxiliaries, for example so as to enable better dispersion of the dyeing preparation.

Preferred powdered dyeing preparations according to the invention have a bulk density in the range of 300 to 600 g/l (grams/liter), preferably 400 to 550 g/l, and particularly preferably 450 to 500 g/l. The bulk density is preferably determined according to the presently applicable DIN regulation.

As a first essential ingredient, the powdered dyeing preparation used according to the invention comprises at least one oxidation dye precursor, which is preferably selected from one or more developer components and optionally one or more coupler components.

Preferably, at least one oxidation dye precursor is present in a total amount of 0.01 to 80 wt. %, preferably of 0.1 to 60 wt. %, particularly preferably of 0.5 to 45 wt. %, and exceptionally preferably of 0.7 to 30 wt. %, in each case based on the weight of the powdered dyeing preparation.

It may be preferred according to the invention for the developer component to be at least one compound selected from the group consisting of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazole-1-yl)propyl]amine, N,N'-bis-(2-hydroxyethyl)-N,N'-bis-(4-aminophenyl)-1,3-diamino-propane-2-ol, bis(2-hydroxy-5-aminophenyl)methane, 1,3-bis-(2,5-diaminophenoxy)-propane-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, and the physiologically compatible salts thereof.

Preferably, at least one developer component is present in a total amount of 0.01 to 80 wt. %, preferably of 0.1 to 60 wt. %, particularly preferably of 0.5 to 45 wt. %, and exceptionally preferably of 0.7 to 30 wt. %, in each case based on the weight of the powdered dyeing preparation.

Within the scope of oxidative dyeing, coupler components alone do not provide any significant coloration, but always require the presence of developer components. It is therefore preferred according to the invention to additionally use at least one coupler component when using at least one developer component.

According to the invention, preferred coupler components are selected from 3-aminophenol, 5-amino2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl)-amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino) ethanol, 2-({3-(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholine-4-ylphenyl)amino]ethanol, 3-amino-4-(2-methoxyethoxy)-5-methylphenylamine, 1-amino-3-bis-(2-hydroxyethyl)-aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-di hydroxy-4-methylpyridine, 2,6-diaminopyridine, 2,3-diamino-6-methoxypyridine, 3,5-diamino-2,6-dimethoxypyridine, 2.6-dihydroxy-3,4-dimethylpyridine, 3,4-diaminopyridine, 2-(2-methoxyethyl)amino-3-amino-6-methoxypyridine, 2-(4'-methoxyphenyl)amino-3-aminopyridine, 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, or mixtures of these compounds or the physiologically compatible salts thereof.

Preferably, at least one coupler component is present in a total amount of 0.01 to 60 wt. %, preferably of 0.1 to 40 wt. %, particularly preferably of 0.5 to 30 wt. %, and exceptionally preferably of 0.7 to 25 wt. %, in each case based on the weight of the powdered dyeing preparation.

The developer components and coupler components are generally used in approximately equimolar amounts relative to each other. While equimolar amounts have proven to be expedient, a certain excess of individual oxidation dye precursors is not disadvantageous, whereby developer components and coupler component can be present in a mole ratio of 1:0.5 to 1:3, and more particularly 1:1 to 1:2.

Preferred kits according to the invention for oxidatively changing the color of keratin fibers are characterized in that the aforementioned oxidation composition according to the invention, or the preferred oxidation composition according to the invention, and the aforementioned powdered dyeing preparation are present at a weight ratio of the oxidation composition to the powdered dyeing preparation of 6 to 12, particularly preferably of 8 to 11, and exceptionally preferably of 9 to 10.

Particularly preferred kits according to the invention for oxidatively changing the color of keratin fibers are characterized in that the aforementioned oxidation composition according to the invention, or the preferred oxidation composition according to the invention, and the aforementioned powdered dyeing preparation are present at a weight ratio of the oxidation composition to the powdered dyeing preparation of 6 to 12, particularly preferably of 8 to 11, and exceptionally preferably of 9 to 10, wherein the kit does not include any further components that are added to the ready-to-apply dyeing mixture, while components for the pre-treatment or post-treatment of the keratin fibers, such as conditioners or shampoos, may be present in the kit. Further preferred kits according to the invention for oxidatively changing the color of keratin fibers are characterized in that they are composed of an aforementioned oxidation composition according to the invention, or a preferred oxidation composition according to the invention, and an aforementioned powdered dyeing preparation at a weight ratio of the oxidation composition to the powdered dyeing preparation of 6 to 12, particularly preferably of 8 to 11, and exceptionally preferably of 9 to 10.

Preferred methods according to the invention for oxidatively changing the color of keratin fibers are characterized in that the aforementioned oxidation composition and the aforementioned powdered dyeing preparation are mixed with one another at a weight ratio of the oxidation composition to the powdered dyeing preparation of 6 to 12, particularly preferably of 8 to 11, and exceptionally preferably of 9 to 10.

Preferably, at least one developer component is present in a total amount of 0.001 to 15 wt. %, preferably of 0.01 to 10 wt. %, particularly preferably of 0.1 to 8 wt. %, and exceptionally preferably of 0.5 to 4 wt. %, in each case based on the weight of the mixture made of the powdered dyeing preparation and the oxidation composition according to the invention.

It is furthermore preferred that at least one coupler component is present in a total amount of 0.001 to 15 wt. %, preferably of 0.01 to 10 wt. %, particularly preferably of 0.1 to 8 wt. %, and exceptionally preferably of 0.5 to 4 wt. %, in each case based on the weight of the mixture made of the powdered dyeing preparation and the oxidation composition according to the invention.

It is furthermore preferred that at least one oxidation dye precursor is present in a total amount of 0.002 to 30 wt. %, preferably of 0.02 to 20 wt. %, particularly preferably of 0.2 to 16 wt. %, and exceptionally preferably of 1.0 to 8 wt. %, in each case based on the weight of the mixture made of the powdered dyeing preparation and the oxidation composition according to the invention.

As a second essential ingredient, the powdered dyeing preparation used according to the invention comprises at least one pigment that does not permanently and not semi-permanently change the color of the fibers. Within the meaning of the present invention, this shall be understood to mean that the coloration of the hair fibers during the method according to the invention is not brought about by the pigments in the powdered dyeing composition, and that a color effect of the keratin fibers that may be caused by the pigments is not colorfast and will be lost again after rinsing the hair once, for example during rinsing at the end of the method according to the invention, which is to say it is not permanent and not semi-permanent. In contrast, permanent coloration is an oxidative coloration of the keratin fibers, in which the oxidation dye precursors penetrate into the hair and, due to the oxidizing agent, react in the fiber to form oligomeric dye molecules, which due to the size thereof remain in the fiber and have high fastness to rinsing and washing processes, mechanical abrasion and light.

Semi-permanent within the meaning of the present invention are colorations created by way of what are known as substantive dyes, which include cationic direct dye, anionic direct dyes and substantive direct dyes.

The coloration of the keratin fibers by the oxidation dye precursors present in the dyeing preparation is neither influenced nor impaired by the pigments that do not provide permanent coloration.

The role of the pigments that do not provide permanent or semi-permanent coloration is essentially to increase the visual attractiveness of the powdered dyeing preparation for the user. Another essential role of the pigments that do not provide permanent or semi-permanent coloration is to impart approximately the color to the powdered dyeing preparation which is achieved on the keratin fiber by method according to the invention and by the kit according to the invention.

Pigments suitable for the method according to the invention can be selected from all pigments that do not provide permanent or semi-permanent coloration suitable for cosmetic use. Preferred are so-called effect and/or pearlescing pigments, which may be of organic and/or inorganic origin.

The use of inorganic pigments is particularly preferred in the method according to the invention given the excellent light, weather and/or temperature resistance thereof.

The preferred volume median particle size of the, preferably inorganic, pigments is 0.1 µm to 1 mm, particularly preferably 0.5 µm to 120 µm, and exceptionally 10 µm to 80 µm.

Preferred pigments that do not provide permanent or semi-permanent coloration are selected from inorganic pigments, which may be of natural origin. Inorganic color pigments of natural origin can be produced from chalk, red ocher, umbra, green earth, burnt sienna or graphite, for example.

Furthermore, it is possible to use white pigments, such as titanium dioxide or zinc oxide, black pigments, such as iron oxide black, color pigments, such as ultramarine or iron oxide, and fluorescent or phosphorescent pigments as inorganic color pigments, wherein preferably at least one pigment is a colored, non-white pigment. Metal oxides, metal hydroxides and metal oxide hydrates, mixed phase pigments, sulfurous silicates, metal sulfides, complex metal cyanides, metal sulfates, metal chromates and/or metal molybdates are particularly suitable. In particular, preferred color pigments are titanium dioxide (CI 77891), black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI77289), iron blue (ferric ferrocyanide, CI77510) and/or carmine (cochineal).

Suitable effect pigments are preferably understood to mean metal effect pigments, such as bronze pigments.

Further preferred pigments according to the invention that do not provide permanent or semi-permanent coloration are those known as pearlescing pigments. These are usually made of mica flakes, which are coated with one or more metal oxides or metal oxychlorides, such as bismuth oxychloride, wherein this layer is, or these layers are, optionally doped with further metal salts or metal oxides. Natural mica-based and natural mica/metal oxide-oxide pearlescing pigments are preferred according to the invention.

Mica forms part of the phyllosilicates. The most important representatives of these silicates are muscovite, phlogopite, paragonite, biotite, lepidolite, and margarite. To produce the pearlescing pigments in combination with metal oxides, the mica flakes, primarily muscovite or phlogopite, are coated with at least one metal oxide.

As an alternative to natural mica, it is optionally also possible to use synthetic mica coated with one or more metal oxides as the pearlescing pigment. Such suitable pearlescing pigments based on synthetic mica are described in the unexamined patent application WO 2005065632, which is hereby explicitly included by reference.

Particularly preferred pearlescing pigments are based on natural or synthetic mica and are coated with one or more metal oxides.

The color of the respective pigments can be varied by varying the layer thickness of the metal oxide or metal oxides. Examples of particularly suitable pearlescing pigments are commercially available, for example, under the trade names Rona®, Colorona®, Dichrona® and Timiron® from Merck, Ariabel® from Sensient, Prestige® from Eckart Cosmetic Colors, and Sunshine® from Sunstar.

In a preferred embodiment, the powdered dyeing preparation comprises at least one inorganic color, effect and/or pearlescing pigment as the pigment that does not provide (semi-)permanent coloration, which is preferably selected from metal oxides, metal hydroxides, metal oxide hydrates, sulfurous silicates, metal sulfides, complex metal cyanides, metal sulfates, bronze pigments and/or mica-based pigments, which are coated with at least one metal oxide and/or a metal oxychloride.

In a particularly preferred embodiment, the powdered dyeing preparation comprises at least one inorganic color and/or pearlescing pigment, selected from titanium dioxide (CI 77891), black iron oxide (Cl 77499), yellow iron oxide (Cl 77492), red and/or brown iron oxide (Cl 77491), manganese violet (Cl 77742), ultramarine (sodium aluminum sulfosilicates, Cl 77007, Pigment Blue 29), chromium oxide hydrate (CI 77289), iron blue (ferric ferrocyanide, CI 77510) and/or mica pigments coated with one or more metal oxides, as the pigment that does not provide (semi-)permanent coloration.

In particular, powdered dyeing preparations that comprise one or more mica pigments coated with titanium dioxide (CI 77891), black iron oxide (CI 77499), red and/or brown iron oxide (Cl 77491), and/or ultramarine (sodium aluminum sulfosilicates, Cl 77007, Pigment Blue 29) are preferred.

In a preferred embodiment of the method according to the invention or of the kit according to the invention, the powdered dyeing preparation comprises, based on the weight of the powdered dyeing preparation, at least one pigment that does not permanently or semi-permanently change the color of the fibers in a total amount of 1 to 40 wt. %, preferably 3 to 30 wt. %, particularly preferably 5 to 25 wt. %, and in particular 7.5 to 20 wt. %.

In a further particularly preferred embodiment of the method according to the invention or of the kit according to the invention, the powdered dyeing preparation comprises, in each case based on the weight of the powdered dyeing preparation:

at least one oxidation dye precursor in a total amount of 0.01 to 80 wt. %, preferably of 0.1 to 60 wt. %, particularly preferably of 0.5 to 45 wt. %, and exceptionally preferably of 0.7 to 30 wt. %; and at least one pigment that does not permanently or semi-permanently change the color of the fibers in a total amount of 1 to 40 wt. %, preferably 3 to 30 wt. %, particularly preferably 5 to 25 wt. %, and in particular 7.5 to 20 wt. %.

In a further particularly preferred embodiment of the method according to the invention or of the kit according to the invention, the powdered dyeing preparation comprises, in each case based on the weight of the powdered dyeing preparation:

at least one developer component in a total amount of 0.01 to 80 wt. %, preferably of 0.1 to 60 wt. %, particularly preferably of 0.5 to 45 wt. %, and exceptionally preferably of 0.7 to 30 wt. %; and at least one pigment that does not permanently or semi-permanently change the color of the fibers in a total amount of 1 to 40 wt. %, preferably 3 to 30 wt. %, particularly preferably 5 to 25 wt. %, and in particular 7.5 to 20 wt. %.

In a further particularly preferred embodiment of the method according to the invention or of the kit according to the invention, the powdered dyeing preparation comprises, in each case based on the weight of the powdered dyeing preparation:

at least one developer component in a total amount of 0.01 to 80 wt. %, preferably of 0.1 to 60 wt. %, particularly preferably of 0.5 to 45 wt. %, and exceptionally preferably of 0.7 to 30 wt. %; and at least one coupler component in a total amount of 0.01 to 60 wt. %, preferably of 0.1 to 40 wt. %, particularly preferably of 0.5 to 30 wt. %, and exceptionally preferably of 0.7 to 25 wt. %; and at least one pigment that does not permanently or semi-permanently change the color of the fibers in a total amount of 1 to 40 wt. %, preferably 3 to 30 wt. %, particularly preferably 5 to 25 wt. %, and in particular 7.5 to 20 wt. %.

In a further preferred embodiment of the method according to the invention or of the kit according to the invention, the powdered dyeing preparation comprises at least one solid inorganic alkalizing agent. According to the invention, this shall be understood to mean in particular salts or silicates reacting in an alkaline manner in an aqueous environment. Solid inorganic alkalizing agents suitable according to the invention are preferably selected from the group consisting of sodium hydroxide, potassium hydroxide, calcium hydroxide, magnesium hydroxide, magnesium carbonate hydroxide, barium hydroxide, sodium phosphate, potassium phosphate, sodium silicate, sodium metasilicate, potassium silicate, potassium metasilicate, ammonium carbonate, sodium carbonate, potassium carbonate and magnesium carbonate, and mixtures of these alkalizing agents. Sodium silicate, sodium metasilicate and magnesium carbonate hydroxide, and mixtures thereof, are particularly preferred alkalizing agents, mixtures of sodium metasilicate and magnesium carbonate hydroxide being exceptionally preferred. The at least one solid inorganic alkalizing agent is preferably present in a total amount of 10 to 60 wt. %, particularly preferably 20 to 50 wt. %, and exceptionally preferably 25 to 40 wt. %, in each case based on the weight of the powdered dyeing preparation. Since the oxidation compositions according to the invention and the preferred oxidation compositions according to the invention, the dyeing methods according to the invention and the kits according to the invention are optimized for a mixture of the oxidation composition and the powdered dyeing preparation at a weight ratio of the oxidation composition to the powdered dyeing preparation of 6 to 12, particularly preferably of 8 to 11, and exceptionally preferably of 9 to 10, the total amount of solid inorganic alkalizing agents must be selected in such a way that the mixture, which is to say the ready-to-apply dye, has an alkaline pH value, preferably a pH value of 8 to 11.5, particularly preferably a pH value of 8.5 to 11, and exceptionally preferably a pH value of 9.0 to 10.5.

So as to reduce dust formation and improve the flowability of the powdered dyeing preparation, it may be advantageous to add an oil component to the dyeing preparation. In principle, all cosmetic oils that were already mentioned above as being suitable for the oxidation compositions according to the invention and the preferred oxidation compositions according to the invention are suitable for this purpose. The addition of paraffin oil, hydrogenated homopolymers of 1-decene with a degree of polymerization n of 3 to 9 (by the INCI name Polydecene) and ester oils, such as isopropyl myristate, isononyl isononanoate and 2-ethylhexyl stearate to the powdered dyeing preparation has been found to be particularly suitable.

A further embodiment of the first subject matter of the invention is thus characterized in that the dyeing preparation additionally comprises at least one oil, which is preferably selected from paraffin oil, hydrogenated homopolymers of 1-decene with a degree of polymerization n of 3 to 9 and ester oils, and mixtures thereof.

The at least one oil, which is preferably selected from paraffin oil, hydrogenated homopolymers of 1-decene with a degree of polymerization n of 3 to 9 and ester oils, is particularly preferably present in a total amount of 0.01 to 5 wt. %, in particular of 0.05 to 3 wt. %, and particularly of 0.08 to 2.0 wt. %, in each case based on the weight of the powdered dyeing preparation.

Exceptionally preferably, paraffin oil is present in an amount of 0.01 to 5 wt. %, in particular of 0.05 to 3 wt. %, and particularly of 0.08 to 1.0 wt. %, in each case based on the weight of the powdered dyeing preparation.

In a further preferred embodiment of the method according to the invention or of the kit according to the invention, the powdered dyeing preparation comprises at least one ammonium compound, selected from ammonium chloride, ammonium carbonate, ammonium bicarbonate, ammonium sulfate and/or ammonium carbamate, and mixtures of these compounds, preferably ammonium chloride, in a total amount of 1 to 50 wt. %, particularly preferably of 5 to 40 wt. %, and in particular of 15 to 35 wt. %, in each case based on the weight of the powdered dyeing preparation.

Further embodiments according to the invention of the oxidation composition, of the kit, and of the dyeing method are characterized in that neither the oxidation composition nor the powdered dyeing preparation comprises a polymer that is substituted with at least two C8 to C30 alkyl groups. Such polymers, which preferably represent associative thickeners, have proven to be disadvantageous in certain instances for the dripping properties of the ready-to-apply dye.

What was said above with respect to the oxidation compositions according to the invention and the preferred oxidation compositions according to the present invention, and with respect to the powdered dyeing preparations used according to the invention applies, mutatis mutandis, with respect to further preferred embodiments of the kit according to the invention.

What was said above with respect to the oxidation compositions according to the invention and the preferred oxidation compositions according to the present invention, and with respect to the powdered dyeing preparations used according to the invention applies, mutatis mutandis, with respect to further preferred embodiments of the method according to the invention.

The ready-to-apply dye of the method according to the invention is preferably produced by combining the oxidation composition according to the invention, or the preferred oxidation composition according to the invention, with a powdered dyeing preparation used according to the invention in a reclosable container, and subsequently mixing these.

In the subsequent method step, the ready-to-apply dye is distributed on the keratin fibers. In the method for changing the color of human hair, the ready-to-apply agent is distributed directly on the scalp hair of the user. The distribution preferably takes place manually. For this purpose, the user removes the ready-to-apply agent from the mixing container, preferably the reclosable container, by ladling or pouring the same onto the hand and subsequently distributing the agent on the scalp hair, and preferably working the same in. Preferably, direct contact between the ready-to-apply dye and the hands is avoided through the use of suitable gloves, such as disposable gloves, for example made of latex.

The ready-to-apply dye then remains on the fibers to be treated for a time period of 1 to 60 minutes. The time period preferably ranges from 10 to 45 minutes, and particularly preferably 20 to 30 minutes.

The application temperatures can range between 15 and 40° C. If necessary, it is also possible to set a higher or precisely defined temperature during the residence time of the agent on the fibers, including by means of external heat sources. It is particularly preferred to support the change in color by way of physical measures. For this reason, methods according to the invention in which the use is enhanced by the action of heat, IR radiation and/or UV radiation during the residence time may be preferred.

After the residence time has lapsed, the ready-to-apply dye or the remaining dye is removed in the last method step by rinsing the same off the fibers to be treated. For this purpose, fibers are rinsed with water and/or an aqueous surfactant preparation. Usually, warm water having a temperature of 20° C. to 40° C. is used for this purpose, or an appropriately temperature-controlled aqueous surfactant preparation. Optionally, further treatment steps may follow, such as the application of a leave-on or rinse-off conditioner, a further dyeing step, such as the coloring or lightening of strands of hair, styling of the hair and/or drying of the hair.

Examples

The following preparations were produced. Table 1 displays examples of powdered dyeing preparations; Table 2 displays one example of an oxidation composition according to the invention. Unless indicated otherwise, the quantity information is provided in wt. %, in each case based on the weight of the individual composition.

1) Powdered dyeing preparations (Table 1)

| Raw materials | I | II | III | IV | V | VI |
|---|---|---|---|---|---|---|
| Sodium metasilicate FE anhydrous | 22.73 | 22.73 | 22.73 | 22.73 | 22.73 | 22.73 |
| Magnesium carbonate hydroxide | 9.15 | 9.15 | 13.77 | 9.10 | 9.10 | 11.40 |
| Perfume | 0.60 | 0.60 | 0.60 | 0.60 | 0.60 | 0.60 |
| Paraffinum liquidum | 1.65 | 1.65 | 1.65 | 1.65 | 1.65 | 1.65 |
| p-toluylene diamine sulfate | 17.60 | 14.3 | 1.50 | 4.79 | 3.56 | 1.97 |
| Resorcinol | 5.73 | 4.91 | 1.25 | 1.57 | 0.99 | 0.22 |
| 3-aminophenol | 2.40 | 1.85 | 0.65 | 0.37 | 0.30 | 0.06 |
| 2,4-diaminophenoxy ethanol 2HCl | 1.53 | 0.76 | 2.40 | | | |
| 4,5-diamino-1-(2-hydroxyethyl)pyrazole sulfate | | | | 5.10 | | |
| 2-methylresorcinol | | | | 0.20 | 0.17 | 0.18 |
| 2-amino-3-hydroxypyridine | | | | 0.34 | | |
| 2,7-dihydroxynapthalene | | | | | | 0.27 |
| 4-chlororesorcinol | | | | | 0.43 | 0.48 |
| Ariabel ® Blue | | | | 4.50 | | |
| Prestige ® Fire Red | | | | 4.50 | | |
| Colorona ® Blackstar Gold | | 13.60 | | | 11.40 | 11.40 |
| Colorona ® Mica Black | 13.60 | | | | | |
| Colorona ® Precious Gold | | | | | | 9.10 |
| Timiron ® Diamond MP 149 | 4.50 | 4.50 | 4.50 | 4.50 | 4.50 | 4.50 |
| Ammonium chloride | | | to make up to 100 | | | |
| Color of the powdered dyeing preparation | black | dark brown | red-violet | brown | brown | golden |

TABLE 2

2) Oxidation composition according to the invention

| Raw material | E1 |
|---|---|
| Cetearyl alcohol | 4.50 |
| Laureth-23 | 0.80 |
| EDTA Na$_2$ | 0.15 |
| 1,2-propylene glycol | 1.00 |
| Sodium cetearyl sulfate | 0.75 |
| Disodium pyrophosphate | 0.30 |
| Hydroxyethyl cellulose | 0.35 |
| Apricot kernel oil | 0.50 |
| Sodium benzoate | 0.04 |
| Hydrogen peroxide (aqueous, 50%) | 6.00 (or 3.00) |
| Phosphoric acid | 0.02 |
| Water | to make up to 100 |

3) List of the Raw Materials Used

Ariabel® Blue (INCI name: Cl 77007 (Ultramarin S), Silicic acid aluminum sodium salt, sulfurized, Pigment Blue 29), Sensient; Prestige® Fire Red (INCI name: Mica, Cl 77491 (Iron Oxides)), Eckart Cosmetic Colors; Colorona® Blackstar Gold (INCI name: Mica, Cl 77499 (Iron Oxides), Merck; Colorona® Mica Black (INCI name: Cl 77499 (Iron Oxides) Mica, Cl 77891 (Titanium oxides)), Merck; Colorona® Precious Gold (INCI name: Mica, Cl 77891 (Titanium oxides), Silica, Cl 77499 (Iron Oxides), SnO), Merck; Timiron® Diamond MP 149 (INCI name: Mica, Cl 77891 (Titanium oxides)), Merck.

4) Coloring Results 11 g of the powdered color-changing preparation I, or 11 g of the powdered color-changing preparation VI, was mixed in each case with 100 g of the oxidation composition according to the invention in a reclosable mixing container by vigorous uninterrupted shaking (40 times).

The ready-to-apply product from preparation I had a black color, while the ready-to-apply product from preparation VI had a golden color. Each of the products was removed from the containers by cupping the hand and evenly distributed on two identical strands of hair (Alkino).

The respective ready-to-apply agent remained on the strands of hair for a residence time of 30 minutes at room temperature (20° C.).

Thereafter, the remaining agent was rinsed off the strands of hair for approximately 2 minutes using lukewarm water (25° C.), and the strands were dried with a towel. Even, lasting and brilliant colorations of high color intensity and chromaticity were obtained. The strand of hair dyed proceeding from preparation I had a black coloration. The strand of hair dyed proceeding from preparation VI had a golden blond coloration.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A kit for oxidatively changing the color of keratin fibers, comprising two compositions that are separate from one another, wherein one of the two compositions is an oxidation composition, said oxidation composition comprising:
   50 to 96 wt. % water:
   0.5 to 20 wt. % hydrogen peroxide;
   at least one linear saturated 1-alkanol having 12 to 30 carbon atoms in a total amount of 2.7 to 6 wt. %;
   at least one polyethylene glycol ether of a linear saturated C12-C22 alkanol having 15 to 30 ethylene oxide units in the molecule, in a total amount of 0.3 to 1 wt. %;
   at least one anionic surfactant in a total amount of 0.3 to 1 wt. %;
   at least one cellulose ether in a total amount of 0.1 to 0.5 wt. %; and
   at least one oil in a total amount of 0.1 to 0.5 wt. %;
wherein all quantity information is based on the weight of the oxidation composition, and
one of the two compositions is a powdered dyeing preparation, which comprises at least one oxidation dye precursor and at least one pigment that does not permanently or semi-permanently change the color of the fibers.

2. A kit according to claim 1, wherein neither the oxidation composition nor the powdered dyeing preparation comprises a polymer that is substituted with at least two C8 to C30 alkyl groups.

3. A kit according to claim 1, wherein the powdered dyeing preparation further comprises at least one ammonium compound selected from the group consisting of ammonium chloride, ammonium carbonate, ammonium bicarbonate, ammonium sulfate, ammonium carbamate, and mixtures thereof, and wherein the at least one ammonium compound is present in a total amount of 1 to 50 wt. % based on the weight of the powdered dyeing preparation.

4. A kit according to claim 1, wherein the oxidation composition has a pH value in the range of 2.5 to 5.5 and a viscosity in the range of 1500 to 3500 mPa·s.

5. A kit according to claim 1, wherein the powdered dyeing preparation furthermore comprises at least one solid inorganic alkalizing agent selected from the group consisting of sodium hydroxide, potassium hydroxide, calcium hydroxide, magnesium hydroxide, magnesium carbonate hydroxide, barium hydroxide, sodium phosphate, potassium phosphate, sodium silicate, sodium metasilicate, potassium silicate, potassium metasilicate, ammonium carbonate, sodium carbonate, potassium carbonate and magnesium carbonate, and mixtures thereof, in a total amount of 10 to 60 wt. % based on the weight of the powdered dyeing preparation.

6. A method for oxidatively changing the color of keratin fibers, including:
providing an oxidation composition, comprising
   50 to 96 wt. % water,
   0.5 to 20 wt. % hydrogen peroxide,
   at least one linear saturated 1-alkanol having 12 to 30 carbon atoms in a total amount of 2.7 to 6 wt. %,
   at least one polyethylene glycol ether of a linear saturated C12-C22 alkanol having 15 to 30 ethylene oxide units in the molecule, in a total amount of 0.3 to 1 wt. %,
   at least one anionic surfactant in a total amount of 0.3 to 1 wt. %,
   at least one cellulose ether in a total amount of 0.1 to 0.5 wt. %, and
   at least one oil in a total amount of 0.1 to 0.5 wt. %,
wherein all quantity information is based on the weight of the oxidation composition;
providing a powdered dyeing preparation, which comprises at least one oxidation dye precursor and at least one pigment that does not permanently change the color of the fibers;
producing a mixture of the aforementioned oxidation composition and the aforementioned powdered dyeing preparation at a weight ratio of the oxidation composition to the powdered dyeing preparation of 6 to 12;
immediately thereafter, distributing the ready-to-apply agent on the fibers;
leaving the agent on the fibers for a time period of 1 to 60 minutes;
and thereafter
rinsing the remaining agent from the fibers and optionally drying the hair.

7. The method according to claim 6, wherein the oxidation composition has a pH value in the range of 2.5 to 5.5 and a viscosity in the range of 1500 to 3500 mPa·s.

8. The method according to claim 6, wherein the mixture composed of the oxidation composition and the powdered dyeing preparation has a pH value of 8 to 11.5.

9. A kit according to claim 1, wherein the at least one linear saturated 1-alkanol having 12 to 30 carbon atoms is selected from the group consisting of myristyl alcohol, cetyl alcohol, stearyl alcohol, arachidyl alcohol and behenyl alcohol, and mixtures thereof.

10. A kit according to claim 1, wherein the at least one polyethylene glycol ether is selected from the group consisting of polyethylene glycol ethers of lauryl alcohol, myristyl alcohol and cetyl alcohol, each having 15 to 30 ethylene oxide units in the molecule.

11. A kit according to claim 10, wherein the at least one polyethylene glycol is laureth-23.

12. A kit according to claim 1, wherein the at least one anionic surfactant is selected from the sodium salts of fatty alcohol sulfates.

13. A kit according to claim 12, wherein the at least one anionic surfactant is selected from sodium cetyl sulfate, sodium stearyl sulfate and sodium cetyl/stearyl sulfate mixtures.

14. A kit according to claim 1, wherein the at least one cellulose ether is selected from the group consisting of hydroxyethyl cellulose, hydroxypropyl cellulose, hydroxypropyl methyl cellulose, methyl hydroxyethyl cellulose and mixtures thereof.

15. A kit according to claim 1, wherein the at least one oil is selected from the group consisting of $C_{18}$ to $C_{30}$ isoparaffins, $C_8$ to $C_{16}$ isoparaffins, 1,3-bis(2-ethylhexyl)cyclohexane, benzoic acid esters of linear or branched $C_{8-22}$ alkanols, fatty alcohols having 6 to 30 carbon atoms, which are unsaturated, or branched and saturated, or branched and unsaturated, triglycerides of linear or branched, saturated or unsaturated, optionally hydroxylated $C_{8-30}$ fatty acids, dicarboxylic acid esters of linear or branched $C_2$ to $C_{10}$ alkanols, esters of linear or branched saturated or unsaturated fatty alcohols having 2 to 30 carbon atoms with linear or branched saturated or unsaturated fatty acids having 2 to 30 carbon atoms, which may be hydroxylated, addition products of 1 to 5 propylene oxide units to monohydric or polyhydric $C_{8-22}$ alkanols, addition products of at least 6 ethylene oxide and/or propylene oxide units to monohydric or polyhydric $C_{3-22}$ alkanols, $C_8$ to $C_{22}$ fatty alcohol esters of monovalent or polyvalent $C_2$ to $C_7$ hydroxycarboxylic acids, symmetric, asymmetric or cyclic esters of carbonic acid with $C_{3-22}$ alkanols, $C_{3-22}$ alkane diols or $C_{3-22}$ alkane triols, esters of dimers of unsaturated $C_{12}$ to $C_{22}$ fatty acids (dimeric fatty acids) with monohydric linear, branched or cyclic $C_2$ to $C_{18}$ alkanols or with polyhydric linear or branched $C_2$ to $C_6$ alkanols, silicone oils, and mixtures of the aforementioned oils.

* * * * *